US00PP15327P2

(12) United States Plant Patent
Klemm

(10) Patent No.: US PP15,327 P2
(45) Date of Patent: Nov. 16, 2004

(54) ***GERANIUM* PLANT NAMED 'KLEP02102'**

(50) Latin Name: *Pelargonium peltatum*
Varietal Denomination: KLEP02102

(75) Inventor: Nils Klemm, Stuttgart (DE)

(73) Assignee: Klemm & Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 10/783,353

(22) Filed: Feb. 21, 2004

(51) Int. Cl.[7] ..... A01H 5/00
(52) U.S. Cl. ..... Plt./332
(58) Field of Search ..... Plt./332

*Primary Examiner*—Kent Bell
(74) *Attorney, Agent, or Firm*—C. A. Whealy

(57) ABSTRACT

A new and distinct cultivar of Ivy *Geranium* plant named 'KLEP02102', characterized by its vigorous plant habit; freely branching habit; early flowering habit; red purple-colored double flowers arranged in umbels; and good tolerance to rain, wind and high temperatures.

1 Drawing Sheet

Botanical classification/cultivar designation: *Pelargonium peltatum* cultivar KLEP02102.

BACKGROUND OF THE INVENTION

The present invention relates to a new and distinct cultivar of *Geranium* plant, botanically known as *Pelargonium peltatum*, and hereinafter referred to by the name 'KLEP02102'.

The new Ivy *Geranium* is a product of a planned breeding program conducted by the Inventor in Stuttgart, Germany. The objective of the breeding program was to develop new Ivy *Geraniums* with uniform and trailing plant habit and interesting flower and foliage colors.

The new Ivy *Geranium* originated from a cross-pollination made by the Inventor in 1998 of a proprietary selection of *Pelargonium peltatum* identified as code number PM 005, not patented, as the female, or seed, parent with the *Pelargonium peltatum* cultivar Kleblue, disclosed in U.S. Plant patent application Ser. No. 09/250,014, now abandoned, as the male, or pollen, parent. The cultivar KLEP02102 was discovered and selected by the Inventor as a flowering plant within the resulting progeny from this cross-pollination in a controlled environment in Stuttgart, Germany, in 1999.

Asexual reproduction of the new cultivar by terminal cuttings taken in a controlled environment in Stuttgart, Germany since 2000 has shown that the unique features of this new Ivy *Geranium* are stable and reproduced true to type in successive generations of asexual reproduction.

SUMMARY OF THE INVENTION

The following traits have been repeatedly observed and are determined to be the unique characteristics of 'KLEP02102'. These characteristics in combination distinguish 'KLEP02102' as a new cultivar and distinguish it from other known Ivy *Geranium* cultivars:

1. Vigorous plant growth habit.
2. Freely branching habit.
3. Early flowering habit.
4. Red purple-colored double flowers arranged in umbels.
5. Good tolerance to wind, rain and high temperatures.

Compared to plants of the female parent selection, plants of the new Ivy *Geranium* are more freely branching and have shorter internodes. In addition, flowers of plants of the new Ivy *Geranium* have more petaloids than flowers of plants of the female parent selection. Plants of the new Ivy *Geranium* and the male parent, the cultivar Kleblue, differ primarily in flower color as plants of the cultivar Kleblue have violet-colored flowers.

Plants of the new Ivy *Geranium* can be compared to plants of the cultivar Klerobright, not patented. In side-by-side comparisons conducted in Stuttgart, Germany, plants of the new Ivy *Geranium* differed from plants of the cultivar Klerobright in the following characteristics:

1. Plants of the new Ivy *Geranium* were not as vigorous as plants of the cultivar Klerobright.
2. Plants of the new Ivy *Geranium* had shorter internodes than plants of the cultivar Klerobright.
3. Leaves of plants of the new Ivy *Geranium* had a less distinct zonation pattern than leaves of plants of the cultivar Klerobright.
4. Plants of the new Ivy *Geranium* and the cultivar Klerobright differed in flower color as plants of the cultivar Klerobright had bright red-colored flowers.
5. Plants of the new Ivy *Geranium* flowered earlier than plants of the cultivar Klerobright.

BRIEF DESCRIPTION OF THE PHOTOGRAPH

The accompanying colored photograph illustrates the overall appearance of the new cultivar, showing the colors as true as it is reasonably possible to obtain in colored reproductions of this type. Flower and foliage colors in the photograph may differ slightly from the color values cited in the detailed botanical description, which accurately describe the colors of the new Ivy *Geranium*. The photograph comprises a side perspective view of a typical flowering plant of 'KLEP02102' grown in a container.

DETAILED BOTANICAL DESCRIPTION

Plants of the cultivar KLEP02102 have not been observed under all possible environmental conditions. The phenotype may vary somewhat with variations in environment, such as temperature and light intensity, without, however, any variance in genotype.

The aforementioned photograph, following observations, and averaged measurements describe plants that were planted in January in Stuttgart, Germany, and grown under commercial practice in a glass-covered greenhouse with day temperatures ranging from 18 to 22° C., night temperatures ranging from 14 to 17° C. and light levels ranging from 20,000 to 60,000 lux. Plants were pinched once during the growing period. The photograph and botanical description were taken about 15 weeks after planting rooted young plants.

In the following description, color references are made to The Royal Horticultural Society Colour Chart, 1995 Edition, except where general terms of ordinary dictionary significance are used.

Botanical classification: *Pelargonium peltatum* cultivar KLEP02102.

Parentage:

*Female parent.*—Proprietary selection of *Pelargonium peltatum* identified as code number PM 005, not patented.

*Male parent.*—*Pelargonium peltatum* cultivar Kleblue, disclosed in U.S. Plant patent application Ser. No. 09/250,014, abandoned.

Propagation:

*Type cutting.*—Terminal vegetative cuttings.

*Time to initiate roots.*—Summer: About 10 days at 22° C. Winter: About 11 days at 18 to 20° C.

*Time to produce a rooted young plant.*—Summer: About 17 days at 22° C. Winter: About 18 days at 18 to 20° C.

*Root description.*—Fine and white in color.

*Rooting habit.*—Freely branching.

Plant description:

*General appearance.*—Trailing plant habit; uniform; plants roughly spherical in shape; densely foliated.

*Growth and branching habit.*—Moderately vigorous. Freely branching, about four to five lateral branches per plant.

*Plant height* (*to top of flower umbels*).—About 24 to 28 cm.

*Plant height* (*to top of foliar plane*).—About 16 to 22 cm.

*Plant width.*—About 18 to 22 cm.

*Lateral branches.*—Length: About 8 to 10 cm. Internode length: About 2.0 to 2.5 cm. Texture: Slightly pubescent. Color: 137C.

*Foliage description.*—Arrangement: Alternate, simple. Quantity of leaves per lateral branch: About six to eight. Length: About 5 cm. Width: About 7 cm. Shape: Reniform with lobation. Apex: Rounded. Base: Peltate. Margin: Entire. Venation pattern: Palmate. Texture, upper and lower surfaces: Rough. Color: Developing foliage, upper surface: 137B. Developing foliage, lower surface: 137C. Fully expanded foliage, upper surface: 137A. Fully expanded foliage, lower surface: 137C. Venation, upper surface: 137C. Venation, lower surface: 137D. Zonation pattern: Distance from margin to outer edge of zone: About 2 cm. Width: About 8 mm. Zone color: 147A. Petiole: Length: About 3.5 cm. Diameter: About 2 mm. Color: 137D.

Flower description:

*Flower arrangement.*—Red purple-colored flowers arranged in rounded hemispherical umbels arising from apical leaf axils. Umbels displayed above the foliage on upright peduncles. Flowers rounded in form. Umbels persistent, flowers not persistent. Flowers not fragrant.

*Quantity of flowers.*—Freely flowering habit; at full flower, plants have at least about five to six open and developing umbels with about 10 to 15 flowers and flower buds per umbel.

*Flowering season.*—Year-round under greenhouse conditions. In the garden, flowering is continuous from spring until fall, with flowering heaviest during periods when night temperatures are 15 to 20° C.

*Time to flower.*—Early flowering; plants start flowering about 84 to 88 days after planting rooted young plants.

*Flower longevity.*—Flowers last about four to eight days on the plant.

*Umbel size.*—Height: About 8 cm. Diameter: About 6 to 10 cm.

*Flower size.*—Diameter: About 3 to 3.5 cm. Depth (height): About 2 cm.

*Flower buds.*—Length: About 8 to 12 mm. Diameter: About 5 to 6 mm. Shape: Elliptical. Color: 139C.

*Petals.*—Quantity per flower: About 22–26. Length: About 2 cm. Width: About 1 cm. Shape: Obovate. Apex: Rounded. Base: Attenuate. Margin: Entire. Texture, upper and lower surfaces: Satiny, smooth. Color: When opening, upper surface: 52A. When opening, lower surface: 52B. Fully opened, upper surface: 57A; color towards base 52D. Fully opened, lower surface: 52B; color towards base 52D. Venation, upper and lower surfaces: 57A.

*Petaloids.*—Quantity per flower: One to about five. Length: About 3 to 10 mm; irregular in size. Width: About 1 to 4 mm; irregular in size. Shape: Variable, irregular. Apex: Mostly rounded. Base: Attenuate. Margin: Mostly entire. Texture, upper and lower surfaces: Satiny, smooth. Color: When opening, upper surface: 52A. When opening, lower surface: 52B. Fully opened, upper surface: 57A; towards the base, 52D. Fully opened, lower surface: 52B; towards the base 52D. Venation, upper and lower surfaces: 57A.

*Sepals.*—Quantity per flower: Five, arranged in a single whorl. Length: About 5 to 8 mm. Width: About 3 to 6 mm. Shape: Elliptical. Apex: Acute. Margin: Entire. Texture, upper and lower surfaces: Rough. Color, upper surface: 139C. Color, lower surface: 139D.

*Peduncle* (*umbel stem*).—Length: About 12 to 16 cm. Diameter: About 4 mm. Angle: Erect. Strength: Moderate to strong. Texture: Slightly pubescent; rough. Color: 139C.

*Pedicel* (*individual flower stem*).—Length: About 2.0 to 2.2 cm. Diameter: About 1 to 1.5 mm. Angle: Erect. Strength: Strong. Texture: Slightly pubescent; rough. Color: 139C.

*Reproductive organs.*—Androecium: Anther quantity per flower: Five. Anther length: About 3 mm. Anther shape: Ovate. Anther color: 57D. Pollen amount: Moderate. Pollen color: 54D. Gynoecium: Pistil quantity per flower: One. Pistil length: About 6 mm. Stigma shape: Five-parted, star-shaped. Stigma color: 54D. Style length: About 4 mm. Style color: 54D. Ovary color: 149D. Seed/fruit: Seed and fruit production has not been observed.

Disease/pest resistance: Plants of the new Ivy *Geranium* have not been observed to be resistant to pathogens and pests common to Ivy *Geraniums*.

Weather tolerance: Plants of the new Ivy *Geranium* have been observed to tolerate rain, wind, and temperatures from about 10 to 30° C.

It is claimed:

1. A new and distinct cultivar of Ivy *Geranium* plant named 'KLEP02102', as herein illustrated and described.

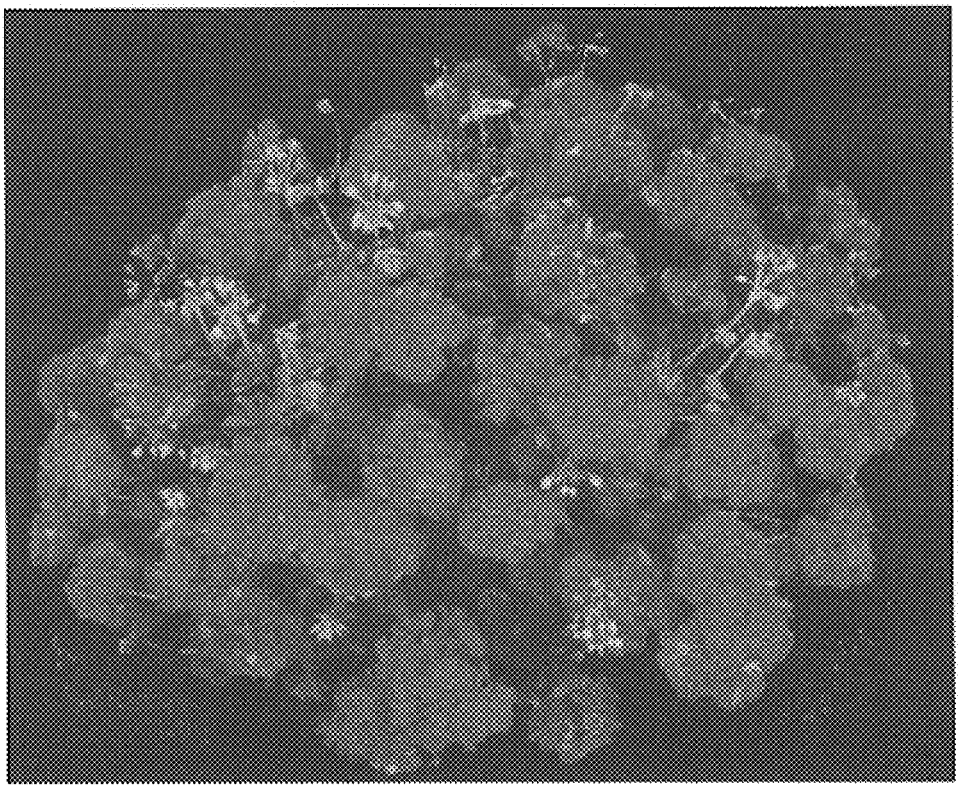

* * * * *